(12) United States Patent
Shimada et al.

(10) Patent No.: US 12,389,967 B2
(45) Date of Patent: Aug. 19, 2025

(54) EYELASH EXTENSION ADHESIVE

(71) Applicants: Katsura Shimada, Ibaraki (JP); Hitoshi Uchida, Tokyo (JP)

(72) Inventors: Katsura Shimada, Ibaraki (JP); Hitoshi Uchida, Tokyo (JP)

( * ) Notice: Subject to any disclaimer, the term of this patent is extended or adjusted under 35 U.S.C. 154(b) by 706 days.

(21) Appl. No.: 17/785,202

(22) PCT Filed: Dec. 11, 2020

(86) PCT No.: PCT/JP2020/046337
§ 371 (c)(1),
(2) Date: Jun. 14, 2022

(87) PCT Pub. No.: WO2021/125093
PCT Pub. Date: Jun. 24, 2021

(65) Prior Publication Data
US 2023/0038661 A1   Feb. 9, 2023
US 2023/0329381 A9   Oct. 19, 2023

(30) Foreign Application Priority Data

Dec. 20, 2019   (JP) ................................. 2019-230642

(51) Int. Cl.
| | | |
|---|---|---|
| *A61G 5/02* | (2006.01) | |
| *A41G 5/02* | (2006.01) | |
| *A61K 8/37* | (2006.01) | |
| *A61K 8/55* | (2006.01) | |
| *A61Q 1/10* | (2006.01) | |
| *A61Q 5/00* | (2006.01) | |
| *C08F 120/18* | (2006.01) | |

(52) U.S. Cl.
CPC . *A41G 5/02* (2013.01); *A61K 8/37* (2013.01)

(58) Field of Classification Search
CPC ... A41G 5/02; A61K 8/37; A61K 8/35; A61K 8/40; A61K 8/55; A61K 8/81; C08F 120/18; C08F 220/1806; C08F 220/1809; C08F 220/1811; C08F 222/102; C08F 222/103; C08F 222/104; C08F 222/1061; C08F 222/1065; C08K 3/013; C08K 2003/2265; C09J 133/08; C09J 4/00; C09J 4/06; C09J 11/04; C09J 133/06; A61Q 1/10; A61Q 5/00
See application file for complete search history.

(56) References Cited

FOREIGN PATENT DOCUMENTS

| | | |
|---|---|---|
| JP | 2010-202532 A | 9/2010 |
| JP | 2019-056095 A | 4/2019 |
| JP | 2019-513712 A | 5/2019 |
| JP | 2019-085366 A | 6/2019 |

*Primary Examiner* — Jeffrey T. Palenik
(74) *Attorney, Agent, or Firm* — Edwin S. Flores; Daniel J. Chalker; Chalker Flores, LLP

(57) ABSTRACT

Provided is an eyelash extension adhesive comprising the following components (a) and (b): (a) a monofunctional monomer of formula (I) wherein $R^1$ represents a hydrogen atom or a methyl group, and $R^2$ to $R^6$ each independently represent a hydrogen atom or a C1 to C6 alkyl group, and (b) a photopolymerization initiator. The eyelash extension adhesive is excellent in durability and water resistance, can adhere easily to eyelashes even in a wet state, and is very useful as a photopolymerizable adhesive for eyelash extension attachment not including a cyanoacrylate compound.

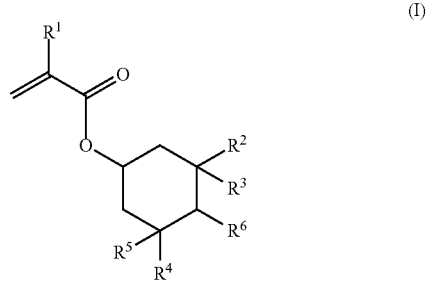

(I)

3 Claims, 1 Drawing Sheet

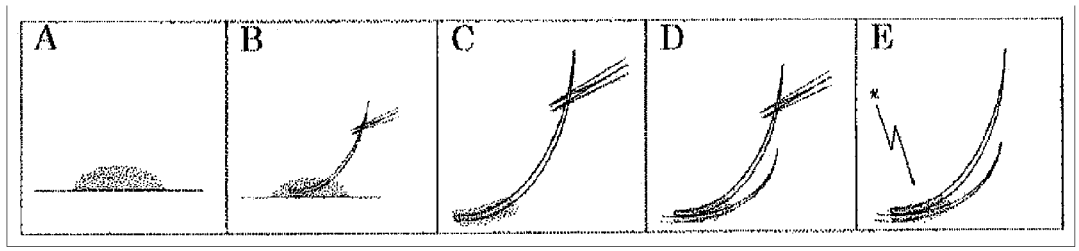

EYELASH EXTENSION ADHESIVE

CROSS-REFERENCE TO RELATED APPLICATIONS

This application is the National Stage of International Application No. PCT/JP2020/046337, filed on Dec. 11, 2020 claiming the priority of JP 2019-230642, filed on Dec. 20, 2019, the content of each of which is incorporated by reference herein.

TECHNICAL FIELD

The present invention relates to a photopolymerizable adhesive for eyelash extension attachment that is excellent in durability and water resistance, that can adhere easily to eyelashes even in a wet state, and that is not including a cyanoacrylate compound. The present application is an application, the priority of which is based on Japanese Patent Application No. 2019-230642 filed on Dec. 20, 2019.

BACKGROUND ART

False eyelashes have been used for a long time in methods for imparting length and volume to eyelashes and producing more beautiful and attractive eyes. Such false eyelashes are used by putting together a plurality of artificial eyelashes directly onto user's eyelids, and can impart length and volume to user's eyelashes. However, the false eyelashes adhere directly to the skin of the user and offer a poor feeling of wearing, and in some cases, might irritate the skin, and aesthetic problems remain.

By contrast, a method called eyelash extension (hereinafter, referred to as an "eyelash ext."), which allows directly bonding, to real eyelashes, artificial eyelash prepared into a shape substantially equivalent to that of real eyelashes has been practiced in recent years (patent document 1). Unlike false eyelashes, this eyelash ext. is not directly bonded to the eyelids, but is bonded directly to eyelashes using a special adhesive, and therefore offers a good feeling of wearing. Another feature of the eyelash ext. is that it can impart length and volume to eyelashes more naturally than false eyelashes, and can be left on for approximately 1 month.

False eyelashes are removed every time and disposable in most cases because an adhesive is attached directly to the eyelids. By contrast, the eyelash ext. is typically left on eyelashes for a certain period of time. As described above, since the eyelash ext. is always worn on eyelashes, it is preferred that the eyelash ext. should not come off from the real eyelashes by face washing or bathing in daily life.

Adhesives supplemented with a cyanoacrylate-based monomer such as ethyl cyanoacrylate or butyl cyanoacrylate have been used in the eyelash ext. (patent document 2). Such a cyanoacrylate compound is a compound that reacts with moisture in the air to quickly initiate polymerization reaction, and is used as a so-called instantaneous adhesive.

As described above, since the cyanoacrylate compound has high reactivity and immediately initiates polymerization reaction through moisture contained in the air or real eyelashes, the time for real eyelashes to wear artificial eyelash (hereinafter, referred to as an operation time) has limitations.

The curing time of the cyanoacrylate-based adhesive is influenced by humidity and temperature. Therefore, for making the operation time constant, it is necessary to make the temperature and humidity of the treatment environment constant, leading to poor usability.

In addition to the problems described above, the cyanoacrylate compound itself has mucous membrane irritation and furthermore has the property of diffusing monomer vapor around a cured product during curing reaction. This monomer vapor might adhere to the surrounding mucous membrane and skin of the eye and cause retinitis, conjunctivitis and dermatitis. Another problem thereof is the risk of producing an aldehyde compound by the hydrolysis of the cyanoacrylate cured product.

For the eyelash extension, a technique called single lash is generally used in which one artificial eyelash is bonded to one real eyelash. On the other hand, a technique called volume lash has been carried out in recent years in which a plurality of artificial eyelashes are bundled in a fan shape and attached to one real eyelash (patent document 3).

In the volume lash, a plurality of artificial eyelashes are bundled into a fan shape, held in this shape with tweezers, and attached to a real eyelash with an adhesive. In this respect, the bundle must be held on the real eyelash, until the curing of the adhesive is completed, such that the fan shape does not collapse. This is a difficult challenge to liquid adhesives, such as cyanoacrylate-based adhesives, the curing time of which is difficult to control.

In light of these problems of cyanoacrylate-based adhesives, photopolymerizable adhesives for eyelash ext. not including cyanoacrylate have been proposed in recent years. Patent document 1 describes Examples in which a specific (meth)acrylate monomer or (meth)acrylamide monomer and a poly functional monomer were used in combination. Patent document 2 describes an adhesive comprising a specific (meth)acrylate monomer and a urethane oligomer used in combination.

However, as a result of conducting replication study on the contents of patent documents 1 and 2, it was found that the adhesive can adhere to dry hair such as hair of the head, but is less likely to adhere to eyelashes or has low adhesion durability even if successfully adhering thereto. In the case of using a specific monomer, an event was seen in which a cured product after curing absorbed water and underwent white discoloration. This whitening event impairs the aesthetics of eyelash ext.

Such an adhesive is less likely to adhere to eyelashes presumably due to water present on the surface or in the inside of hair. Since eyelashes grow at the edge of eyelids, the eyelashes are always in a highly humid state due to tears and have a predominantly high water content as compared with other human hairs such as hair of the head. In eyelash ext. treatment, washing is generally performed for the purpose of removing makeup dirt, etc. Thus, eyelash surface before treatment easily falls into a wet state by water. Since the cyanoacrylate-based adhesive described above causes polymerization reaction through reaction with water, a certain amount of water often becomes no serious problem. For the photopolymerizable adhesive not including cyanoacrylate, water is an adhesion inhibitory factor and becomes a serious problem.

In order to mitigate the influence of moisture, a possible method is to add a hydrophilic monomer miscible with water, such as 2-hydroxyethyl methacrylate, into adhesive composition. However, use of the hydrophilic monomer relatively enhances the hydrophilicity of a cured product and therefore facilitates water absorption and whitening, which are not preferred.

SUMMARY OF THE INVENTION

Object to be Solved by the Invention

An object of the present invention is to provide a photopolymerizable adhesive for eyelash extension attachment that is excellent in durability and water resistance and can adhere easily to hair even in a wet state.

Means to Solve the Object

The present inventors have conducted diligent studies to attain the object and consequently found that a photopolymerizable adhesive containing a monofunctional monomer of a formula given below adheres easily to even wet hair and has both of high adhesion durability and water resistance.

Surprisingly, the monomer of the formula given below, albeit being hydrophobic, adheres easily to wet hair without combined use with a hydrophilic monomer, and is also excellent in adhesion durability.

Specifically, the Present Invention is as Follows.

(1) An eyelash extension adhesive comprising the following components:
(a) a monofunctional monomer of formula (I):

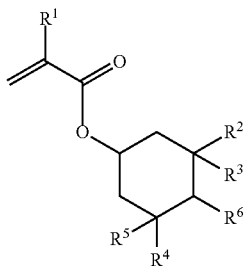

(I)

wherein $R^1$ represents a hydrogen atom or a methyl group, and $R^2$ to $R^6$ each independently represent a hydrogen atom or a C1 to C6 alkyl group, and
(b) a photopolymerization initiator.
(2) The eyelash extension adhesive according to (1), further comprising one or more components selected from
(c) a polyfunctional monomer of formula (II):

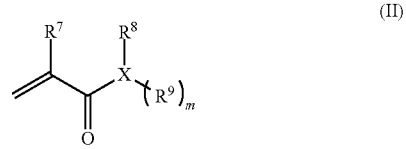

(II)

wherein $R^7$ represents a hydrogen atom or a methyl group, X represents an oxygen atom or a nitrogen atom, at least one of $R^8$ and $R^9$ represents an organic group containing one or more polymerizable groups, and the other optionally represents a hydrogen atom, when X is an oxygen atom, m=0, and when X is a nitrogen atom, m=1,
(d) a polymerization inhibitor,
(e) a colorant,
(f) a thickener, and
(g) a filler.
(3) The eyelash extension adhesive according to (2), wherein iron oxide selected from the group consisting of ferrous oxide, ferric oxide (colcothar) and triiron tetraoxide (black iron oxide) is used as the colorant.

Effect of the Invention

The eyelash extension adhesive of the present invention can circumvent curing time or operability problems or even the risks of mucous membrane irritation, by-product aldehyde compounds, and the like in cyanoacrylate-based adhesives. The eyelash extension adhesive of the present invention has convenient operability, can adhere easily to even eyelashes in a wet state or highly humid eyelashes, and is excellent in durability and water resistance, and as such, practically has very high usefulness.

Furthermore, the adhesive of the present invention can also be used as an extension adhesive for body hair other than eyelashes (e.g., hair (hair of the head) and eyebrows).

BRIEF DESCRIPTION OF DRAWING

FIG. 1 is a diagram showing the step of treating an eyelash extension with the adhesive of the present invention.

MODE OF CARRYING OUT THE INVENTION

Hereinafter, the present invention will be described in detail.

The component (a) is a monofunctional monomer of formula (I) described above and is a component that defines curability, adhesiveness, and the solubility of a cured product. In the present application, the "monofunctional monomer" means a monomer having only one reactive functional group in the structure of one monomer molecule.

In formula (I), $R^1$ represents a hydrogen atom or a methyl group, and $R^2$ to $R^6$ each independently represent a hydrogen atom or a C1 to C6 alkyl group. The C1 to C6 alkyl group means a linear or branched alkyl group having 1 to 6 carbon atoms. In one aspect of the present invention, $R^2$ to $R^6$ each independently represent a hydrogen atom or a C1 to C4 alkyl group. Examples of the C1 to C6 alkyl group include, but are not limited to, a methyl group, an ethyl group, a n-propyl group, an isopropyl group, a n-butyl group, a sec-butyl group, an isobutyl group, a tert-butyl group, a n-pentyl group, and a n-hexyl group.

Examples of the component (a) include cyclohexyl (meth)acrylate, 3-methylcyclohexyl (meth)acrylate, 4-methylcyclohexyl (meth)acrylate, 4-tert-butylcyclohexyl (meth)acrylate, 3,3-dimethylcyclohexyl (meth)acrylate, 3,4-dimethylcyclohexyl (meth)acrylate, 3-methyl-4-tert-butylcyclohexyl (meth)acrylate, 3,3-dimethyl-4-tert-butylcyclohexyl (meth)acrylate, 3,5-dimethylcyclohexyl (meth)acrylate, 3,5-dimethyl-4-tert-butylcyclohexyl (meth)acrylate, 3,3,4-trimethylcyclohexyl (meth)acrylate, 3,3,5-trimethylcyclohexyl (meth)acrylate, 3,3,5-trimethyl-4-tert-butylcyclohexyl (meth)acrylate, 3,3,5,5-tetramethylcyclohexyl (meth)acrylate, 3,3,5,5-tetramethyl-4-tert-butylcyclohexyl (meth)acrylate, 3,3,4,5-tetramethylcyclohexyl (meth)acrylate, and 3,3,4,5,5-pentamethylcyclohexyl (meth)acrylate. Cyclohexyl (meth)acrylate, 4-t-butylcyclohexyl (meth)acrylate, and 3,3,5-trimethylcyclohexyl (meth)acrylate are preferred from the viewpoint of availability and light curability. Among them, 3,3,5-trimethylcyclohexyl (meth)acrylate is more preferred. The term "(meth)acrylate" can include both acrylate and methacrylate.

The reason why the monomer having the structure of formula (I), albeit being hydrophobic, is excellent in close contact to wet hair is not clear. This monomer presumably pushes away water present on hair surface and infiltrates into the gaps between cuticle structures, though the details are unknown.

An existing photopolymerization initiator can be used as the photopolymerization initiator as the component (b). In consideration of use near the eyes, a photopolymerization initiator having absorption in the range of near-ultraviolet to visible light regions is preferred, and a photopolymerization initiator capable of exciting polymerization reaction at a wavelength of 350 nm or larger is more preferred.

Examples of the photopolymerization initiator that satisfies these conditions include (bis)acylphosphine oxides, ketals, and α-diketones.

Examples of the acylphosphine oxides in the (bis)acylphosphine oxides for use as the photopolymerization initiator include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and (2,5,6-trimethylbenzoyl)-2,4,4-trimethylpentylphosphine oxide.

Among these (bis)acylphosphine oxides, 2,4,6-trimethylbenzoyldiphenylphosphine oxide, 2,4,6-trimethylbenzoylmethoxyphenylphosphine oxide, and bis(2,4,6-trimethylbenzoyl)phenylphosphine oxide are particularly preferred.

Examples of the ketals for use as the photopolymerization initiator include benzyl dimethyl ketal and benzyl diethyl ketal.

Examples of the α-diketones for use as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among them, camphorquinone is particularly preferred from the viewpoint of having the maximum absorption wavelength in the visible light region.

Among these photopolymerization initiators, at least one member selected from the group consisting of (bis)acylphosphine oxides, α-diketones, and ketals is preferably used. As a result, an adhesive that is excellent in light curability in the visible and near-ultraviolet regions and exhibits sufficient light curability even if any light source of a halogen lamp, a light-emitting diode (LED), and a xenon lamp is used, is obtained.

The polyfunctional monomer as the component (c) of formula (II) is a compound having a plurality of (meth)acrylic groups in a single molecule, and a compound that is dissolved in the component (a) at room temperature can be used without any problem.

At least one of $R^8$ and $R^9$ in the polyfunctional monomer as the component (c) represents an organic group containing one or more polymerizable groups, and the other optionally represents a hydrogen atom.

In the present application, the "polymerizable group" means a group that is contained in a certain compound capable of producing a polymerized product (polymer) with an identical compound or another compound, and can form the polymerized product. Examples of the polymerizable group include, but are not limited to, an alkenyl group such as a vinyl group and an allyl group, an epoxy group, a carboxyl group, a hydroxy group, and an amino group.

In the present application, the "organic group" means a population of atoms constituting a group of an organic compound. Examples of the organic group include, but are not limited to, an alkyl group (e.g., a methyl group and an ethyl group), an alkenyl group (e.g., a vinyl group and an allyl group), an alkoxy group (e.g., a methoxy group and an ethoxy group), an alkenyloxy group (e.g., a vinyloxy group and an allyloxy group), an aryl group (e.g., a phenyl group and a naphthyl group), an arylalkyl group (e.g., a benzyl group and a phenethyl group), an acyl group (e.g., an aldehyde group (formyl group), an acetyl group, a propionyl group, a benzoyl group, and an acrylyl group), a benzenesulfonyl group, —OH, —COOH, —NH$_2$, —NO$_2$, and —CN.

Examples of the commercially available and obtainable component (c) include ethylene glycol di(meth)acrylate, diethylene glycol di(meth)acrylate, triethylene glycol di(meth)acrylate, tetraethylene glycol di(meth)acrylate, propylene glycol di(meth)acrylate, dipropylene glycol di(meth)acrylate, tripropylene glycol di(meth)acrylate, 1,6-hexanediol di(meth)acrylate, neopentyl glycol di(meth)acrylate, bisphenol A di(meth)acrylate, bisphenol F di(meth)acrylate, dimethylol tricyclodecane di(meth)acrylate, trimethylolpropane tri(meth)acrylate, ethoxylated trimethylolpropane tri(meth)acrylate, ditrimethylolpropane tetra(meth)acrylate, ethoxylated ditrimethylolpropane tetra(meth)acrylate, pentaerythritol tri(meth)acrylate, pentaerythritol tetra(meth)acrylate, ethoxylated pentaerythritol tetra(meth)acrylate, dipentaerythritol hexa(meth)acrylate, polyester poly(meth)acrylate, 2,2,4-trimethyl hexamethylene bis(2-carbamoyloxyethyl) di(meth)acrylate and urethane (meth)acrylate oligomers.

Ethoxylated trimethylolpropane tri(meth)acrylate, ethoxylated pentaerythritol tetra(meth)acrylate, polyester poly(meth)acrylate, and a urethane (meth)acrylate oligomer are preferred from the viewpoint of light curability, and toughness and elasticity that can be imparted to a cured product. Among them, polyester poly(meth)acrylate and a urethane (meth)acrylate oligomer are preferred. The term "(meth)acrylate" can include both acrylate and methacrylate.

The polymerization inhibitor as the component (d) is used for improvement in the preservation stability of a product and the prolongation of the duration of use. A hindered phenolic compound or an existing polymerization inhibitor, such as BHT, HQ, MEHQ, 2,2'-methylenebis-(6-tertiary butyl-p-cresol), or 6-tertiary butyl-2,4-xylenol, may be used. 2,2'-Methylenebis-(6-tertiary butyl-p-cresol) and 6-tertiary butyl-2,4-xylenol are more preferred in relation to solubility or coloring.

The colorant as the component (e) is used for the natural look of the adhesive used. An existing pigment such as carbon black, a dye capable of dissolving a resin, and carbon fiber, etc. may be used. Among them, iron oxide which rarely influences light curability and has strong coloring power, particularly, ferrous oxide, ferric oxide (colcothar) and triiron tetraoxide (black iron oxide), are more preferred.

The thickener as the component (f) is used for adjusting the viscosity of the adhesive and conferring sticking to ext. hairs and real eyelashes.

The substance used may be any substance that can thicken a monomer, and hydrophobized silica particles are preferred. Examples of the hydrophobized silica particles include Aerosil R972, Aerosil R974, Aerosil R976, Aerosil R812, Aerosil R104, and Aerosil R106.

The filler as the component (g) is used for improvement in the strength of a cured product and improvement in operability. The substance used can be an existing silica filler, a glass filler, or the like which can be used without any problem. A hydrophobized filler is preferred in view of dispersibility in a monomer and the strength of a cured product.

The adhesive may optionally comprise other components including a fragrance, a photopolymerization sensitizer such as isopropyl thioxanthone, a photopolymerization aid such as a thiol compound, an elastomer such as polybutene, a redox polymerization catalyst such as peroxide or a redox polymerization promoter such as aromatic amine, aliphatic amine, or an organic metal complex, a solvent (e.g., water and an alcohol) that is not involved in polymerization, and an oil component such as liquid paraffin.

[Preparation of Adhesive]

The component (a) and optionally the component (c) are mixed, then the component (b) is added to the mixture, and further other components are added thereto and mixed to prepare an adhesive.

The amount of the component (a) used can be freely selected without impairing adhesion performance, and is at least 20 wt % or more, preferably 30 wt % or more, based on the total amount of the monomer from the viewpoint of adhesion durability and the strength of a cured product. The amount of the component (b) is at least 0.1 wt % or more, preferably in the range of 1 to 10 wt %, based on the total amount of the monomer. If the amount of the component (b) falls below 0.1 wt %, there is a risk of markedly reducing curability. If the amount of the component (b) exceeds 10 wt %, there is a risk of reducing the strength of a cured product. The amount of the component (c) is at least 75 wt % or less, preferably 40 wt % or less, based on the total amount of the monomer. If the amount of the component (c) exceeds 75 wt %, there is a risk of markedly reducing adhesiveness to hair.

[Use Method]

A method for using the product of the present invention will be described in detail.

(1) First, a necessary amount of the adhesive is placed on a glue plate or the like (FIG. 1A).

(2) The base of an ext. hair sandwiched with tweezers is dipped in the adhesive so that the adhesive adheres to the ext. hair (FIGS. 1B and 1C).

(3) The ext. hair is set to a real eyelash (FIG. 1D).

(4) The adhesive is cured by exposure to light (FIG. 1E).

In carrying out the single lash and the volume lash, the adhesion operation is the same as above except for the presence or absence of operation of bundling a plurality of ext. hairs beforehand.

EXAMPLES

Hereinafter, the present invention will be further described with reference to Examples. However, the present invention is not limited thereby.

In Examples, the hydrophilicity of the monomer used and the initial adhesiveness to eyelashes, adhesion durability, water resistance, and close contact with wet human hair of a prepared adhesive were evaluated.

Hydrophilicity: Each monomer was mixed with water in equal volumes. A sample that was transparent and dissolved was given o, and a sample that exhibited separation or white turbidity was given x.

Initial adhesiveness to eyelashes: An adhesive was applied so as to involve a PBT ext. hair of φ0.15 mm and 11 mm in length together with a washed eyelash of a test subject. The adhesive was cured by exposure to light at 405 nm. Immediately thereafter, face washing was performed. Determination was as follows: a sample that came off easily was given x, and a sample that did not come off was given o.

Adhesion durability: A PBT ext. hair of φ0.15 mm and 6 to 13 mm in length for single lash or a bundle of three PBT ext. hairs of φ0.05 mm and 10 to 13 mm in length for volume lash was bonded to 25 to 120 sites per subject with an adhesive so as to involve the ext. hair or the bundle together with a washed eyelash of a test subject. The adhesive was cured with light at 405 nm. Then, the test subject lived ordinary life, and the number of ext. hairs remaining 2 weeks later was observed. Determination was as follows: a sample with 50% or more ext. hairs remaining was given o, and a sample with less than 50% ext. hairs remaining was given x. However, a test piece that came off was observed when recoverable, and included in the number of ext. hairs remaining if the eyelash itself was lost due to molt.

Water resistance: An adhesive was applied so as to involve a PBT ext. hair of φ0.15 mm and 11 mm in length together with hair. The adhesive was cured by exposure to light at 405 nm, then dipped in purified water of 40° C. for 3 days, and then dried, and the surface state was observed. Determination was as follows: a sample with no change was given o, and a whitened sample was given x.

Close contact with wet human hair: Hair was misted with water. While the water droplets stayed on the hair surface, an adhesive was applied so as to involve a PBT ext. hair of φ0.15 mm and 11 mm in length together with the hair. The adhesive was cured by exposure to light at 405 nm. Determination was as follows: a sample that did not come off easily when pulled out using tweezers was given o, and a sample that came off when pulled out using tweezers was given x.

The results are shown in Tables 1 and 2. The unit of the amount of each component added represents part by weight.

Abbreviation

TMCHA: 3,3,5-trimethylcyclohexyl acrylate
TBCHA: 4-tert-butylcyclohexyl acrylate
CHMA: cyclohexyl methacrylate
NMMA: N-(methoxymethyl)methacrylamide
DMAA: N, N-dimethylacrylamide
IBXA: isobornyl acrylate
THFMA: tetrahydrofurfuryl methacrylate
THFA: tetrahydrofurfuryl acrylate
ACMO: acryloylmorphorine
PHEA-2: phenol EO-modified acrylate (EO≈2 mol)
HEAA: N-(2-hydroxyethyl) acrylamide
HEMA: 2-hydroxyethyl methacrylate
HEA: 2-hydroxyethyl acrylate
ATM-35E: ethoxylated pentaerythritol tetraacrylate
Eb-450: polyester acrylate (hexafunctional)
Eb-1830: polyester acrylate (hexafunctional)
8001G: urethane acrylate oligomer (bifunctional)
QC-7100: urethane acrylate oligomer (bifunctional)
QC-8100: urethane acrylate oligomer (bifunctional)
Eb-8465: urethane acrylate oligomer (trifunctional)
TPO: 2,4,6-trimethylbenzoyldiphenylphosphine oxide
819: bis(2,4, 6-trimethylbenzoyl)phenylphosphine oxide
MF-15: carbon fiber (length≈15 μm)
Sol-B5: Solvent Black 5
FeO: ferrous oxide
$Fe_3O_4$: black iron oxide (triiron tetraoxide)
$Fe_2O_3$: colcothar (ferric oxide)
R711: Aerosil R711
R974: Aerosil R974
GM27884: silane-treated glass filler (particle size≈4.0 μm)
HPS3500: silane-treated silica filler (particle size≈4.0 μm)
MDP-S: 2,2'-methylenebis-(6-tertiary butyl-p-cresol)
tBXy: 6-tertiary butyl-2,4-xylenol

TABLE 1

| | Compound name | Hydro-philicity | Example 1 | Example 2 | Example 3 | Example 4 | Example 5 |
|---|---|---|---|---|---|---|---|
| (a) | TMCHA | X | 2.4000 | 2.4000 | — | — | — |
| | TBCHA | X | — | — | 2.4000 | 2.4000 | 2.4000 |
| | CHMA | X | — | — | — | — | — |
| | NMMA | X | — | — | — | — | — |
| | IBXA | X | — | — | — | — | — |
| | ACMO | X | — | — | — | — | — |
| | PHEA-2 | X | — | — | — | — | — |
| | DMAA | ○ | — | — | — | — | — |
| | THFMA | ○ | — | — | — | — | — |
| | THFA | ○ | — | — | — | — | — |
| | HEAA | ○ | — | — | — | — | — |
| | HEMA | ○ | — | — | — | — | — |
| | HEA | ○ | — | — | — | — | — |
| (b) | TPO | | 0.3000 | — | 0.3000 | — | — |
| | 819 | | — | 0.2500 | — | 0.2500 | 0.2500 |
| (c) | ATM-35E | | 0.0500 | — | 0.0500 | — | — |
| | Eb-450 | | — | 0.1000 | — | 0.1000 | — |
| | Eb-1830 | | 0.0500 | — | 0.0500 | — | — |
| | 8001G | | — | 0.3000 | — | 0.3000 | — |
| | QC-7100 | | 0.4000 | 0.9000 | 0.4000 | 0.8000 | — |
| | QC-8100 | | 0.3000 | — | 0.3000 | — | — |
| | Eb-8465 | | 0.2000 | — | 0.2000 | — | — |
| (d) | MDP-S | | 0.0050 | 0.0050 | 0.0050 | 0.0050 | 0.0050 |
| | tBXy | | 0.0045 | 0.0050 | 0.0045 | 0.0050 | 0.0050 |
| (e) | MF-15 | | — | 0.0100 | — | 0.0100 | — |
| | Sol-B5 | | 0.0005 | — | 0.0005 | — | — |
| | FeO | | — | — | — | — | — |
| | Fe3O4 | | — | — | — | — | — |
| | Fe2O3 | | — | — | — | — | — |
| (f) | R711 | | 0.0500 | 0.0500 | 0.0500 | 0.0500 | 0.0800 |
| | R974 | | 0.0400 | 0.0400 | 0.0400 | 0.0400 | 0.0600 |
| (g) | GM27884 | | 3.7000 | — | 3.7000 | — | — |
| | HPS3500 | | — | 3.3900 | — | 3.3900 | 4.6000 |
| | Initial adhesiveness | | ○ | ○ | ○ | ○ | ○ |
| Adhesion durability | Single (the number of ext. hairs remaining/the number of ext. hairs worn) | | 203/240 | 185/220 | 98/130 | 81/120 | 26/50 |
| | Volume (the number of ext. hairs remaining/the number of ext. hairs worn) | | 181/200 | 169/190 | 75/110 | 67/100 | 27/50 |
| | Residual rate (%) | | 87.27% | 86.34% | 72.08% | 67.27% | 53.00% |
| | Determination | | ○ | ○ | ○ | ○ | ○ |
| | Water resistance | | ○ | ○ | ○ | ○ | ○ |
| | Close contact with wet human hair | | ○ | ○ | ○ | ○ | ○ |

| | Compound name | Hydro-philicity | Example 6 | Example 7 | Example 8 | Example 9 | Example 10 |
|---|---|---|---|---|---|---|---|
| (a) | TMCHA | X | — | — | 2.4000 | 2.4000 | 2.4000 |
| | TBCHA | X | — | — | — | — | — |
| | CHMA | X | 2.4000 | 1.0000 | — | — | — |
| | NMMA | X | — | — | — | — | — |
| | IBXA | X | — | — | — | — | — |
| | ACMO | X | — | — | — | — | — |
| | PHEA-2 | X | — | — | — | — | — |
| | DMAA | ○ | — | — | — | — | — |
| | THFMA | ○ | — | — | — | — | — |
| | THFA | ○ | — | — | — | — | — |
| | HEAA | ○ | — | — | — | — | — |
| | HEMA | ○ | — | — | — | — | — |
| | HEA | ○ | — | — | — | — | — |
| (b) | TPO | | 0.3000 | — | — | — | — |
| | 819 | | — | 0.2500 | 0.2500 | 0.2500 | 0.2500 |
| (c) | ATM-35E | | 0.0500 | — | — | — | — |
| | Eb-450 | | — | 0.2000 | 0.1000 | 0.1000 | 0.1000 |
| | Eb-1830 | | 0.0500 | — | — | — | — |
| | 8001G | | — | 0.6000 | 0.3000 | 0.3000 | 0.3000 |
| | QC-7100 | | 0.4000 | 1.8000 | 0.9000 | 0.9000 | 0.9000 |
| | QC-8100 | | 0.3000 | — | — | — | — |
| | Eb-8465 | | 0.2000 | — | — | — | — |
| (d) | MDP-S | | 0.0050 | 0.0050 | 0.0050 | 0.0050 | 0.0050 |
| | tBXy | | 0.0045 | 0.0050 | 0.0050 | 0.0050 | 0.0050 |
| (e) | MF-15 | | — | 0.0100 | — | — | — |
| | Sol-B5 | | 0.0005 | — | — | — | — |
| | FeO | | — | — | 0.0200 | — | — |
| | Fe3O4 | | — | — | — | 0.0200 | — |
| | Fe2O3 | | — | — | — | — | 0.0300 |
| (f) | R711 | | 0.0500 | 0.0500 | 0.0500 | 0.0500 | 0.0500 |
| | R974 | | 0.0400 | 0.0400 | 0.0400 | 0.0400 | 0.0400 |

TABLE 1-continued

|  |  |  |  |  |  |  |
|---|---|---|---|---|---|---|
| (g) | GM27884 | 3.7000 | — | — | — | — |
|  | HPS3500 | — | — | 3.3900 | 3.3900 | 3.3900 |
|  | Initial adhesiveness | ○ | ○ | ○ | ○ | ○ |
| Adhesion durability | Single (the number of ext. hairs remaining/the number of ext. hairs worn) | 65/120 | 41/80 | 98/120 | 85/100 | 61/80 |
|  | Volume (the number of ext. hairs remaining/the number of ext. hairs worn) | 66/130 | 25/50 | 81/100 | 63/80 | 52/60 |
|  | Residual rate (%) | 51.60% | 50.77% | 81.36% | 82.22% | 80.71% |
|  | Determination | ○ | ○ | ○ | ○ | ○ |
|  | Water resistance | ○ | ○ | ○ | ○ | ○ |
|  | Close contact with wet human hair | ○ | ○ | ○ | ○ | ○ |

TABLE 2

|  | Compound name | Hydro-philicity | Comparative Example 1 | Comparative Example 2 | Comparative Example 3 | Comparative Example 4 | Comparative Example 5 |
|---|---|---|---|---|---|---|---|
| (a) | TMCHA | X | — | — | — | — | — |
|  | TBCHA | X | — | — | — | — | — |
|  | CHMA | X | — | — | — | — | — |
|  | NMMA | X | 2.4000 | — | — | — | — |
|  | IBXA | X | — | 2.4000 | — | — | 1.6000 |
|  | ACMO | X | — | — | 2.4000 | — | — |
|  | PHEA-2 | X | — | — | — | 2.4000 | — |
|  | DMAA | ○ | — | — | — | — | 0.8000 |
|  | THFMA | ○ | — | — | — | — | — |
|  | THFA | ○ | — | — | — | — | — |
|  | HEAA | ○ | — | — | — | — | — |
|  | HEMA | ○ | — | — | — | — | — |
|  | HEA | ○ | — | — | — | — | — |
| (b) | TPO |  | 0.3000 | 0.3000 | 0.3000 | 0.3000 | 0.3000 |
|  | 819 |  | — | — | — | — | — |
| (c) | ATM-35E |  | 0.0500 | 0.0500 | 0.0500 | 0.0500 | 0.0500 |
|  | Eb-450 |  | — | — | — | — | — |
|  | Eb-1830 |  | 0.0500 | 0 0500 | 0.0500 | 0.0500 | 0.0500 |
|  | 8001G |  | — | — | — | — | — |
|  | QC-7100 |  | 0.4000 | 0.4000 | 0.4000 | 0.4000 | 0.4000 |
|  | QC-8100 |  | 0.3000 | 0.3000 | 0.3000 | 0.3000 | 0.3000 |
|  | Eb-8465 |  | 0.2000 | 0.2000 | 0.2000 | 0.2000 | 0.2000 |
| (d) | MDP-S |  | 0.0050 | 0.0050 | 0.0050 | 0.0050 | 0.0050 |
|  | tBXy |  | 0.0050 | 0.0050 | 0.0050 | 0.0050 | 0.0050 |
| (e) | MF-15 |  | — | — | — | — | — |
|  | Sol-B5 |  | — | — | — | — | — |
|  | FeO |  | — | — | — | — | — |
|  | Fe3O4 |  | — | — | — | — | — |
|  | Fe2O3 |  | — | — | — | — | — |
| (f) | R711 |  | 0.0500 | 0.0500 | 0.0500 | 0.0500 | 0.0500 |
|  | R974 |  | 0.0400 | 0.0400 | 0.0400 | 0.0400 | 0.0400 |
| (g) | GM27884 |  | 3.7000 | 3.7000 | 3.7000 | 3.7000 | 3.7000 |
|  | HPS3500 |  | — | — | — | — | — |
|  | Initial adhesiveness |  | X | X | X | X | ○ |
| Adhesion durability | Single (the number of ext. hairs remaining/the number of ext. hairs worn) |  | — | — | — | — | 0/25 |
|  | Volume (the number of ext. hairs remaining/the number of ext. hairs worn) |  | — | — | — | — | 0/25 |
|  | Residual rate (%) |  | — | — | — | — | 0.00% |
|  | Determination |  | X | X | X | X | X |
|  | Water resistance |  | X | ○ | ○ | ○ | X |
|  | Close contact with wet human hair |  | X | X | X | X | X |

|  | Compound name | Hydro-philicity | Comparative Example 6 | Comparative Example 7 | Comparative Example 8 | Comparative Example 9 | Comparative Example 10 |
|---|---|---|---|---|---|---|---|
| (a) | TMCHA | X | — | — | — | — | — |
|  | TBCHA | X | — | — | — | — | — |
|  | CHMA | X | — | — | — | — | — |
|  | NMMA | X | — | — | — | — | — |
|  | IBXA | X | 1.6000 | 1.6000 | — | — | — |
|  | ACMO | X | — | — | 2.0000 | 2.0000 | 2.0000 |
|  | PHEA-2 | X | — | — | — | — | — |
|  | DMAA | ○ | — | — | — | — | — |
|  | THFMA | ○ | 0.8000 | — | — | — | — |
|  | THFA | ○ | — | 0.8000 | — | — | — |
|  | HEAA | ○ | — | — | 0.4000 | — | — |
|  | HEMA | ○ | — | — | — | 0.4000 | — |
|  | HEA | ○ | — | — | — | — | 0.4000 |

TABLE 2-continued

| | | | | | | |
|---|---|---|---|---|---|---|
| (b) | TPO | 0.3000 | 0.3000 | 0.3000 | 0.3000 | 0.3000 |
| | 819 | — | — | — | — | — |
| (c) | ATM-35E | 0.0500 | 0.0500 | 0.0500 | 0.0500 | 0.0500 |
| | Eb-450 | — | — | — | — | — |
| | Eb-1830 | 0.0500 | 0.0500 | 0.0500 | 0.0500 | 0.0500 |
| | 8001G | — | — | — | — | — |
| | QC-7100 | 0.4000 | 0.4000 | 0.4000 | 0.4000 | 0.4000 |
| | QC-8100 | 0.3000 | 0.3000 | 0.3000 | 0.3000 | 0.3000 |
| | Eb-8465 | 0.2000 | 0.2000 | 0.2000 | 0.2000 | 0.2000 |
| (d) | MDP-S | 0.0050 | 0.0030 | 0.0050 | 0.0050 | 0.0050 |
| | tBXy | 0.0050 | 0.0050 | 0.0050 | 0.0050 | 0.0050 |
| (e) | MF-15 | — | — | — | — | — |
| | Sol-85 | — | — | — | — | — |
| | FaO | — | — | — | — | — |
| | Fe3O4 | — | — | — | — | — |
| | Fe2O3 | — | — | — | — | — |
| (f) | R711 | 0.0500 | 0.0500 | 0.0500 | 0.0500 | 0.0500 |
| | R974 | 0.0400 | 0.0400 | 0.0400 | 0.0400 | 0.0400 |
| (g) | GM27834 | 3.7000 | 3.7000 | 3.7000 | 3.7000 | 3.7000 |
| | HPS3500 | — | — | — | — | — |
| | Initial adhesiveness | ◯ | ◯ | ◯ | ◯ | ◯ |
| Adhesion durability | Single (the number of ext. hairs remaining/the number of ext. hairs worn) | 0/25 | — | 0/25 | — | 2/25 |
| | Volume (the number of ext. hairs remaining/the number of ext. hairs worn) | — | 0/25 | — | 2/25 | 1/25 |
| | Residual rate (%) | 0.00% | 0.00% | 0.00% | 8.00% | 6.00% |
| | Determination | X | X | X | X | X |
| | Water resistance | X | X | X | X | X |
| | Close contact with wet human hair | X | X | X | X | X |

As shown in Examples 1 to 10 of Table 1, the adhesive prepared using the monomer of general formula 1 (TMCHA, TBCHA, CHMA) is found to be excellent in all of initial adhesiveness, adhesion durability and water resistance and to be closely contacted easily with wet hair. Comparative Examples 1 to 4 showed examples in which, unlike the monomer of general formula 1, a monomer having no cyclohexyl group was used and no hydrophilic monomer was used in combination therewith. The adhesive without the use of a hydrophilic monomer is found to adhere easily to neither eyelashes nor wet hair and to be also inferior in adhesion durability. Comparative Examples 5 to 10 of Table 2 showed examples in which, unlike the monomer of general formula 1, a monomer having no cyclohexyl group was used in combination with a hydrophilic monomer. The combined use with the hydrophilic monomer is found to keep adhesion durability low and to deteriorate water resistance, though improving initial adhesiveness to eyelashes. In Comparative Examples 1 to 10, the monomers used in Examples of patent documents 1 and 2 were used as the component (a).

From these test results, the component (a) having a cyclohexyl group according to the present invention is found not only to have a characteristic chemical structure different from that of the previously disclosed components, but to be excellent in all of initial adhesiveness, adhesion durability and water resistance and to be practically very useful as an eyelash ext. adhesive component.

INDUSTRIAL APPLICABILITY

The eyelash extension adhesive of the present invention has the following characteristics:

(i) There is no need for labor related to the management of a treatment environment temperature and humidity for making a curing time or an operation time constant.

(ii) Since polymerization is completed instantaneously as compared with a conventional cyanoacrylate-based adhesive, the amount of unreacted monomers scattered is drastically reduced. Accordingly, less mucous membrane irritation occurs, and use of the adhesive rarely causes retinitis, conjunctivitis or dermatitis.

(iii) The adhesive of the present invention has convenient operability, a long retention time after curing, and good solubility in a solvent and therefore facilitates detachment operation.

(iv) The adhesive of the present invention can also be used as an extension adhesive for body hair other than eyelashes (e.g., hair (hair of the head) and eyebrows). Thus, the present invention is a very useful invention in the field of cosmetic technology.

PRIOR ART DOCUMENTS

Patent Documents

Patent document 1: Japanese unexamined Patent Application Publication No. 2019-202975

Patent document 2: Japanese unexamined Patent Application Publication No. 2019-56095

Patent document 3: Japanese Patent No. 5955355

The invention claimed is:

1. A method for adhering an extension hair to an eyelash, comprising
   adhering an adhesive to the extension hair,
   setting the extension hair adhered with the adhesive to the eyelash, and
   curing the adhesive by exposure to light,
   wherein the adhesive comprises the following components (a) and (b), and does not comprise a cyanoacrylate compound:

(a) a monofunctional monomer of formula (I):

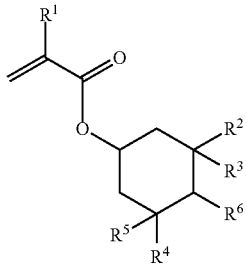

wherein $R^1$ represents a hydrogen atom or a methyl group, and $R^2$ to $R^6$ each independently represent a hydrogen atom or a $C_1$ to $C_6$ alkyl group, and
(b) a photopolymerization initiator.

2. The method according to claim 1, wherein the adhesive further comprises one or more components selected from (c) a polyfunctional monomer of formula (II):

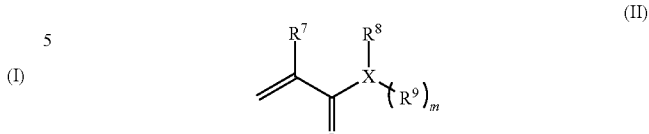

wherein $R^7$ represents a hydrogen atom or a methyl group; X represents an oxygen atom or a nitrogen atom; at least one of $R^8$ and $R^9$ represents an organic group containing one or more polymerizable groups, and the other optionally represents a hydrogen atom;
when X is an oxygen atom, m=0, and when X is a nitrogen atom, m=1,
(d) a polymerization inhibitor,
(e) a colorant,
(f) a thickener, and
(g) a filler.

3. The method according to claim 2, wherein iron oxide selected from the group consisting of ferrous oxide, ferric oxide (colcothar) and triiron tetraoxide (black iron oxide) is used as the colorant.

* * * * *